(12) United States Patent
Shah

(10) Patent No.: US 6,663,646 B1
(45) Date of Patent: *Dec. 16, 2003

(54) **ISOTROPICALLY EXPANSIBLE BALLOON ARTICLES USEFUL IN *IN VIVO* LUMENAL PROCEDURES, AND METHOD OF MAKING SUCH BALLOON ARTICLES**

(76) Inventor: Tilak M. Shah, 104 Lochberry La., Cary, NC (US) 27511

( * ) Notice: Subject to any disclaimer, the term of this patent is extended or adjusted under 35 U.S.C. 154(b) by 371 days.

This patent is subject to a terminal disclaimer.

(21) Appl. No.: 09/695,489

(22) Filed: Oct. 24, 2000

(51) Int. Cl.[7] ............................................. A61M 29/00
(52) U.S. Cl. ...................................................... 606/192
(58) Field of Search ................................. 606/191, 192, 606/194, 198, 195

(56) References Cited

U.S. PATENT DOCUMENTS

| | | | |
|---|---|---|---|
| 3,868,431 A | | 2/1975 | Hutchinson ................. 260/859 |
| 3,976,553 A | * | 8/1976 | Larsen ....................... 428/419 |
| 4,003,382 A | * | 1/1977 | Dyke ......................... 604/103 |
| 4,906,244 A | * | 3/1990 | Pinchuk et al. ............. 606/194 |
| 4,950,239 A | | 8/1990 | Gahara et al. |
| 4,952,357 A | * | 8/1990 | Euteneuer .................... 606/194 |
| 5,002,556 A | * | 3/1991 | Ishida et al. ................ 606/191 |
| 5,439,443 A | * | 8/1995 | Miyata et al. ............... 606/194 |
| 6,261,260 B1 | * | 7/2001 | Maki et al. ............ 604/103.07 |
| 6,291,543 B1 | * | 9/2001 | Shah .......................... 522/162 |
| 6,492,443 B1 | * | 12/2002 | Kodemura et al. ......... 524/114 |

\* cited by examiner

*Primary Examiner*—Michael J. Milano
*Assistant Examiner*—Jessica R Baker
(74) *Attorney, Agent, or Firm*—Steven J. Hultquist; Mimi Yang; Marianne Fuierer

(57) ABSTRACT

A balloon article, e.g., for an in vivo lumenal procedure, formed of a UV cross-linkable polyurethane material that is partially cross-linked to an extent providing a desired expansibility and/or compliant character to the balloon. The degree of cross-linking is selectively modified by the degree of UV exposure to which the balloon article is exposed, and/or the relative proportion of the cross-linking agent, to achieve corresponding product characteristics ranging from semi-compliant to non-compliant polyurethane film properties, including low creep/semi-compliant films.

25 Claims, 2 Drawing Sheets

ISOTROPICALLY EXPANSIBLE BALLOON ARTICLES USEFUL IN IN VIVO LUMENAL PROCEDURES, AND METHOD OF MAKING SUCH BALLOON ARTICLES

BACKGROUND OF THE INVENTION

1. Field of the Invention

The present invention relates to balloon articles and to methodology for making same, in particular a balloon useful for in vivo lumenal medical procedures, having enhanced robustness, expansibility (inflation) and isotropy characteristics, relative to balloons of the prior art.

2. Description of the Related Art

Various balloon articles are in use for cardiovascular and other medical procedures (such as percutaneous transluminal angioplasty, percutaneous transluminal nephrostomy, ureteral dilatation, biliary duct dilatation, percutaneous transluminal renal angioplasty, and the like).

Examples include so-called high pressure balloons for percutaneous transluminal angioplasty treatment applications, in which the balloon is introduced into an arterial lumen to deform (flatten) a blood clot or plaque on an arterial wall surface, as well as balloons that are otherwise stent-deployed into a cardiovascular locus.

High pressure balloons are generally formed of materials such as PET, nylon, Isoplast® and other highly rigid and crystalline polymers whose high pressure strength derives from crystallization of the base of the polymer. Such balloons are pressurized to levels on the order of 6–12 atmospheres (90–180 psi).

Such high pressure balloons of the prior art have the problem attributable to their pre-shaped character that when folded for stent deployment, the folded balloon article forms "wings," i.e., flattened protruberant portions of the balloon, that make it difficult to deploy the balloon in vivo from the stent. Further, because of its floppy, "winged" conformation, the folded balloon article is susceptible to disengaging from the stent, thereby rendering it extremely difficult in some instances to properly position the stent.

Other examples of balloon articles used in the art include so-called low pressure balloons, which are inflated to a pressure on the order of 1–3 psi. Low pressure balloons are used in cardiovascular applications for blocking blood flow, or for removing/blocking a blood clot. In such applications, the balloon is typically bonded to the shaft of a catheter, and after inflation and use, the balloon is readily retracted to an original catheter sleeve shape Low pressure balloons are typically formed of latex. Latex is a superior material for such balloon articles, since it is very soft and flexible in character, has high elongation and good memory characteristics, and exhibits low creep, but latex allergic reaction and susceptibility are increasingly recognized as a major issue confronting the use of latex articles of all types.

Another issue confronting the use of balloon articles for in vivo usage is the asymmetric character of the inflation, An ideal solution to the above-described winging problem associated with high pressure balloons would be the provision of a semi-compliant balloon that has a low profile or sleeve shape that can expand to a desired size (radius), that is amenable to high pressure inflation and that when deflated contracts to a shaft sleeve or an original low profile shape.

In low pressure balloon applications, an ideal solution to the latex allergic reaction and susceptibility issue would involve the availability of another material that is free of the allergenic issues associated with latex, exhibits low creep and high elasticity, and is readily bondable to a catheter shaft. There are otherwise non-allergenic materials that possess high elasticity character, e.g., silicone, but such materials are not easily bonded to the catheter shaft. Other materials exist that are more readily bondable and have good elasticity characteristics, e.g., polyurethanes, but such materials have unsatisfactory creep characteristics.

The aforementioned ideal solutions do not exist in the current state of the art, which continues to seek improvement in balloon articles for cardiovascular and other applications.

SUMMARY OF THE INVENTION

The present invention relates in one aspect to a balloon article comprising a balloon formed of a partially UV-cross-linked polyurethane material.

The invention in another aspect relates to an ultraviolet radiation-crosslinked balloon article formed of a homogeneous composition including a UV-cross-linkable polyurethane material, a cross-linker component that is cross-linkable by free-radical polymerization, and a free-radical source material generating free radicals in exposure to ultraviolet radiation, wherein the homogeneous composition is partially cross-linked by exposure to ultraviolet radiation, and wherein the balloon article is resiliently deformable from and resiliently recoverable to an initial shape of the article.

A still further aspect of the invention relates to a method of fabricating a balloon article for in vivo lumenal use, comprising the steps of: forming a precursor structure for the balloon article of a homogeneous composition including a cross-linkable polyurethane material, a cross-linker component that is cross-linkable by free-radical polymerization, and a free-radical source material generating free radicals in exposure to ultraviolet radiation, and exposing the precursor structure to ultraviolet radiation for sufficient time and under sufficient radiation intensity to partially cross-link the composition, to yield the balloon article.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
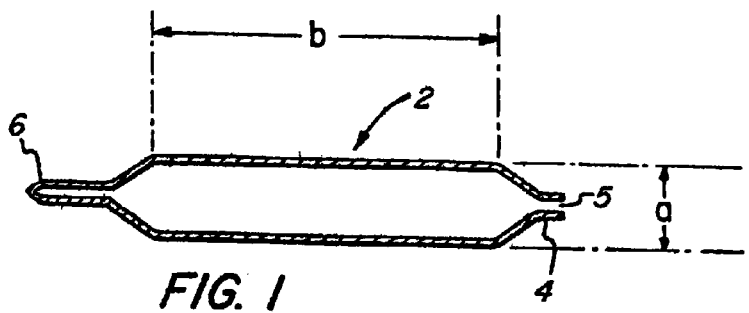
FIG. 1 is a cross-sectional elevation view of a balloon article according to one embodiment of the invention.

The balloon article of the present invention is formed of a UV cross-linkable polyurethane material that is cross-linked to an extent that provides a desired expansibility and/or compliant character to the balloon. The degree of cross-linking that is useful in a given use application can be readily empirically determined without undue effort, by varying the degree of UV exposure to which the balloon article is exposed, or the relative proportion of the cross-linking agent, and assessing the corresponding pressure/extension characteristics of the resulting balloon article.

The balloon article as initially formed may be exposed to UV radiation to provide a balloon product that is controllably expansible and usefully employed in cardiovascular and other medical procedures. The degree of cross-linking can be varied to achieve corresponding product characteristics ranging from semi-compliant to non-compliant polyurethane film properties, including low creep/semi-compliant films.

The balloon of the present invention in such respect represents a fundamental departure from the prior art in the provision of a polyurethane balloon that is only partially cross-linked (i.e., less than all cross-linkable moieties in the film are cross-linked), to provide a product article that has modified properties relative to corresponding uncross-linked or fully cross-linked polyurethane film materials. As a result, film properties can be appropriately varied for a specific end use application, to provide desired compliance (ability of the balloon exterior surface to conform in shape to the confinement opposing it, with semi-compliant film articles being partially conformable to such confinement, and non-compliant film articles being shape-determined independently of the confinement and with an intrinsic shape) and creep characteristics.

Such degree of cross-linking can be readily controlled, by (1) the percentage of cross-linker used in the film-forming composition employed to fabricate the balloon, relative to an amount required for 100% cross-linking, and/or (2) the time of exposure of the balloon film to the UV cross-linking radiation. As mentioned, the degree of cross-linking for a given application may be readily varied and a % cross-linking value can be established that will yield the appropriate desired characteristics of the film.

The balloon article of the invention is readily fabricated from the polyurethane film in any suitable manner, e.g., by blow molding, dip molding, extrusion molding, roto-molding, injection molding, etc. It is possible to form a balloon from component sheets of the polyurethane film, as joined by welding, solvent bonding, etc., but seamless fabrication by any of the seamless fabrication techniques is preferred. The film material is formulated with the amount of cross-linker component appropriate to the specific end-use application.

The film material can be cross-linked by exposing the formed balloon product article to the UV radiation that is effective for inducing free-radical initiated cross-linking of the film. In instances where the balloon is formed by seamed constructions, such as welded film constructions, etc., the film can be exposed to the desired radiation before or after the product article is assembled, e.g., the film stock can be irradiated with UV radiation to partially cross-link the film, or preferably the balloon article can be fabricated and then exposed to the cross-linking UV radiation.

The source of UV radiation can be of any suitable type, as for example a UV cure lamp of conventional design, providing the desired UV radiation spectral characteristics (wavelength within the UV range, intensity/flux characteristics, etc.) and field of radiation exposure (geometric or spatial locus of irradiation).

Preferably, the irradiation is arranged to be uniform over the surface area of the polyurethane film, with the preferred result that the cross-linking density (density of cross-links) throughout the film is substantially uniform. This preferred heterogeneous cross-linking throughout the film provides isotropic film properties on inflation (expansion) of the balloon, so that the radial force exerted by the inflated balloon on the lumenal confinement is circumferentially uniform, over the entire exterior surface of the balloon.

The balloon article of the invention is flexible and yet semicompliant in character, and is expansible to a predetermined shape of the article before inflation and distension of the balloon incident to internal pressurization thereof. By contrast, balloon articles of the prior art experience uncontrolled extension beyond a desired shape, when inflated and distended by internal pressurization.

It will be appreciated that the cross-linking of the polyurethane film in the practice of the invention can be carried out at varied UV radiation exposure times and UV radiation intensities, as necessary or desirable to achieve an ultraviolet radiation-cross-linked balloon article for a specific end use.

The polyurethane film formulation used for the article of the invention includes a polyurethane material, a cross-linker component that is cross-linkable by free-radical polymerization, and a free-radical source material generating free radicals in exposure to ultraviolet radiation.

The polyurethane resin may be of any suitable type that is cross-linkable by UV radiation in formulation with the cross-linker and free-radical UV initiator.

The cross-linker component utilized in the homogeneous composition of the invention likewise may be of any suitable type. Illustrative examples of cross-linkers that can be usefully employed in various embodiments of the invention include compounds containing functional groups such as acryl, (meth) acryl, vinyl, propenyl, butenyl, pentenyl, hexenyl, octenyl, allyl, alkenyloxy, alkenylamino, allyloxy, allylamino, furanyl, phenyl and benzyl groups. The cross-linker desirably contains an ethylenically unsaturated moiety such as vinyl or allyl. Examples of specific cross-linker compounds include trimethylolpropane triacrylate, triallyl isocyanurate, melamine cross-linkers, etc.

The free-radical source material in the homogeneous composition comprises a material generating free-radicals in exposure to ultraviolet radiation. Such free-radical source materials include photoinitiators, such as benzoin, substituted benzoins such as benzoin ethyl ether, benzophenone, benzopheone derivatives, Michler's ketone, alphahydroxyketone, benzildimethylketal, isopropylthioxanthane, dialkoxyacetophenones such as diethoxyacetophenone, acetophenone, benzil, and other derivatives (substituted forms) and mixtures thereof.

The relative amounts of the cross-linker component and free-radical source material relative to the polyurethane material, may be widely varied in the practice of the invention. Particularly suitable compositions may be readily empirically determined by simple formulation and UV irradiation tests to determine the ultimate physical and chemical properties of the final cross-linked material and product article comprising same. In general, the photoinitiator concentration will be in a range of about 0.1% to about 65% by weight, and more specifically and preferably from about 0.2% to about 50% by weight, based on the weight of the cross-linker component.

The photointiator employed in the formulation may be polymer-bound, and may in fact be bound to the polyurethane material.

The cross-linker component is present in the formulation at any suitable concentration. In preferred practice of the invention, the cross-linker has a concentration of from about 1% to about 20% by weight, based on the weight of the polyurethane material present in the formulation.

The polyurethane formulation may also include other ingredients to modify the ultimate properties of the article, as necessary or desirable for a specific end use application.

Fillers or reinforcing materials may be usefully employed in formulations of the present invention to provide enhanced mechanical properties or other specific functional properties, and in some instances to enhance UV radiation curability of the composition.

Preferred fillers include radiopaque fillers such as barium sulfate, bismuth trioxide, bismuth oxychloride, bismuth subcarbonate, tungsten powder, and combinations and compatible blends thereof. Radiopaque fillers have the advantage that they enable the balloon to be readily visualized in the body by fluoroscopic techniques and on x-ray film for therapeutic monitoring and diagnostic radiology.

Alternatively, the polyurethane formulation may include other UV radiation blocking or scattering components, whose concentration will determine the extent of cross-linking in the material of the article subjected to UV radiation.

Among non-radiopaque fillers, a wide variety of other materials may be used for filling or reinforcement of the composition. Preferred fillers include reinforcing silicas, such as fumed silicas, which may be untreated (hydrophobic) or treated to render them hydrophilic in character.

In general, fillers may be employed at any suitable concentration in the cross-linkable composition, but generally are present at concentrations of from about 5 to about 45% by weight, based on the weight of the polyurethane material. Generally, any other suitable mineralic, carbonaceous, glass or ceramic fillers may be potentially advantageously employed. Examples include ground quartz, tabular alumina, diatomaceous earth, silica balloons, calcium carbonate, carbon black, titanium oxide, aluminum oxide, aluminum hydroxide, zinc oxide, glass fibers, etc.

The polyurethane formulation can further include any suitable additives, such as UV stabilizers (e.g., UV stabilizers commercially available from Ciba-Geigy, Inc. under the trademarks Chimassorb and Tinuvin), antioxidants (e.g., those commercially available from Ciba-Geigy, Inc. under the trademark Irganox), colorants, pigments, etc.

The polyurethane formulation of the invention may be prepared in any suitable manner, involving blending or combining the respective polyurethane material, cross-linker and free-radical source ingredients to form a homogeneous composition that subsequently may be processed into a precursor structure, the term "precursor structure" meaning the structure that is exposed to ultraviolet radiation to cross-link the polyurethane material and form the product radiation-cross-linked balloon article.

The polyurethane formulation thus can be prepared by any suitable mixing or blending technique, e.g., agitation by mechanical stirring, sonification treatment, translation through a static mixer device, or in any other suitable manner to achieve a state of homogeneity for the formulation. The formulation can be further melt-blended using a single or twin screw extruder, then pelletized, dried and processed into a specific product.

More generally, the polyurethane formulation can be processed in any suitable conventional manner appropriate to the end use article, e.g., by injection molding, casting, extrusion (e.g., of tubing, profile or film), rotational molding, blow molding, or dip molding, out of solution of the formulation in an appropriate solvent dispersion in water.

In preferred practice for manufacture of balloon articles of appropriate character, the homogeneous polyurethane formulation after its preparation is compounded and pelletized, then formed by extrusion into tubing or other precursor structure.

Once the precursor structure is formed, the surface area of the precursor structure is exposed to UV radiation of suitable intensity for an appropriate period of time. For angiographic balloon structures, the cross-linking can be effected by UV light exposure for a period of 30 seconds to 10 minutes at a radiation intensity of from about 300 microwatts per square centimeter to about 30,000 microwatts per square centimeter. It will be appreciated that there is an inverse correlation of exposure time and UV light intensity, with higher UV intensity generally requiring shorter exposure periods, and vice versa. In some instances, depending on the UV intensity of the radiation to which the precursor structure is exposed, it can be advantageous to employ more restricted radiation intensity values, e.g., in the range of from about 600 to about 26,000 microwatts per square centimeter, or even a narrower range of from about 4,000 to about 20,000 microwatts per square centimeter.

By such cross-linking, the precursor structure is converted to the product article. As a result, the shape of the product balloon article is appropriately "set" by the cross-linking, and the balloon article thereafter will retain "memory" and elastically recover its initial shape when a deforming force is removed from the article subsequent to distension of the article under the applied deforming force.

The UV radiation % cross-linking employed in accordance with the present invention is generally in the range of from about 20% to about 80% of the cross-linkable moieties of the polyurethane material for high pressure (4–6 atmospheres) balloon applications, and in the range of from about 5% to about 50% for low pressure (1–5 psi) balloon applications. Such percentage cross-linking is defined by the formula:

% cross-linking=[(cross-linked sites in a unit amount of the polyurethane material)÷(total cross-linkable sites in the unit amount of the polyurethane material)]×100%

Referring now to the drawings, FIG. 1 is a cross-sectional elevation view of a balloon article 2 according to one embodiment of the present invention comprising a tube 4 with a wall thickness of for example about 0.05 mm. to about 0.5 mm. and an internal diameter of for example about 0.8 mm. to about 10 mm. The tubular body of the balloon is formed in any suitable manner, such as by extrusion of a polyurethane resin formulation containing an ultraviolet radiation-activated cross-linker and a photoinitiator.

After extrusion, one end of the tube is inserted into a mold having an internal configuration corresponding to the external configuration of the desired balloon. The tube 4 is pinched off at one end 6. The mold is heated above the softening temperature of the polyurethane (in the range of about 60° C. to about 150° C.) and a suitable fluid such as nitrogen is used to pressurize and inflate the softened portion of the tube and force the walls thereof into contact with the walls of the mold.

In general, where the balloon is to be used in angioplasty the external diameter, a, of the balloon typically will be of the order of from about 2 mm. to about 4 mm. The overall length, b, of the inflated portion correspondingly will be on the order of about 10 mm. to about 50 mm. The walls of the balloon generally will have an average thickness in the range of from about 0.01 mm. to about 0.2 mm, depending in part on the pressures to which the balloon is to be inflated in actual use. It will be appreciated, however, that these dimensions are illustrative only and that balloon articles of the invention can be widely varied in their dimensional characteristics.

Figure 2:
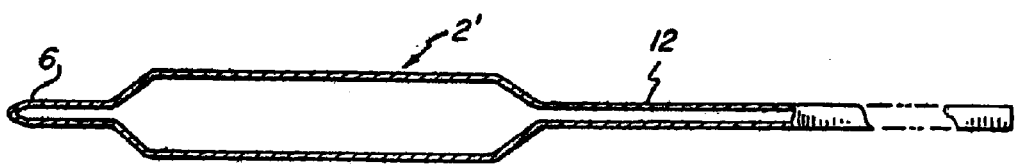
FIG. 2 is a cross-sectional elevation view of a balloon and attached catheter in accordance with another embodiment of the invention.

FIG. 2 is a cross-sectional elevation view of a balloon article 2' of the type shown in FIG. 1 attached on the end of a catheter 12. The catheter is advantageously formed of any of various suitable materials, e.g., polyurethanes available under the trademarks ESTANE and PELLETHANE from B.F. Goodrich and Dow Chemical Company; polyvinyl chloride; styrenic polymers such as KRATON; polyacrylates, polyolefins, polyamides, polyesters, fluoropolymers, silicones, and the like conventionally employed in the art to prepare catheters.

The balloon can also be molded directly onto the end of the catheter if the catheter is made of a same material of construction as the balloon, e.g., by a method of molding analogous to that described above in connection with the embodiment shown in FIG. 1. The tip 6 of the balloon 2' in the embodiment of FIG. 2, is preferably tapered and rounded at its extremity. The balloon and catheter in FIG. 2 are formed as a single, integral unit thus avoiding the necessity to form the balloon and catheter separately and then bond them together.

Nonetheless, the balloon and the catheter can be separately formed and subsequently joined, as an alternative to the integral formation of the balloon and catheter assembly described above. For example, the catheter can be fabricated in any suitable manner, e.g., by extrusion or the like, with the union of the balloon and the distal end of the catheter being achieved by inserting the distal end into the balloon opening to form an overlap as for example on the order of about 2 mm. and thereafter sealing the abutting surfaces to each other using heat welding, solvent welding, ultrasonic welding, hot melt bonding, adhesive bonding using one- or two-part solid adhesives, or other suitable conventional techniques.

Figure 3:
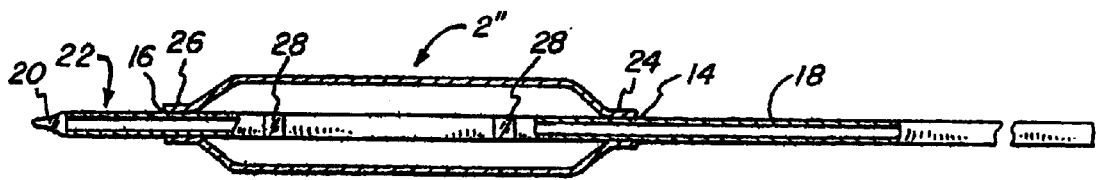
FIG. 3 is a cross-sectional elevation view of a balloon and attached catheter in accordance with yet another embodiment of the invention.

FIG. 3 is a cross-sectional elevation view of a balloon 2" and attached catheter 18 in accordance with yet another embodiment of the invention. The balloon has openings 14 and 16 at each end thereof. A balloon having this configuration is advantageously fabricated from a balloon of the general configuration shown in FIG. 1 by removal of the tip 6 therefrom or, alternatively, such open-ended balloon can be molded directly from a polyurethane formulation of the type discussed above, by injection molding and like conventional techniques.

The balloon is then mounted on catheter 18 by insertion of the tip 20 of catheter 18 into opening 14 and out through opening 16 so that a predetermined portion 22 of the distal end of the catheter 18 protrudes from the balloon. The length of portion 22 can be varied over a wide range depending on the desired use and method of functioning of the balloon catheter so formed. The abutting surfaces of catheter 18 and flanges 24 and 26 of balloon 2" are then bonded.

Catheter 18 is fabricated from any of the polymeric materials described hereinabove. Catheter 18 is provided with radiopaque bands 28 and radiopaque tip 20 fabricated from radiopaque materials such as platinum and gold. These elements serve to monitor by x-ray the location of the tip 20 and the balloon 2" during a medical dilatation procedure and to ensure that the balloon is located in the desired area of an artery or like vessel or duct before the balloon is inflated.

Figure 4:
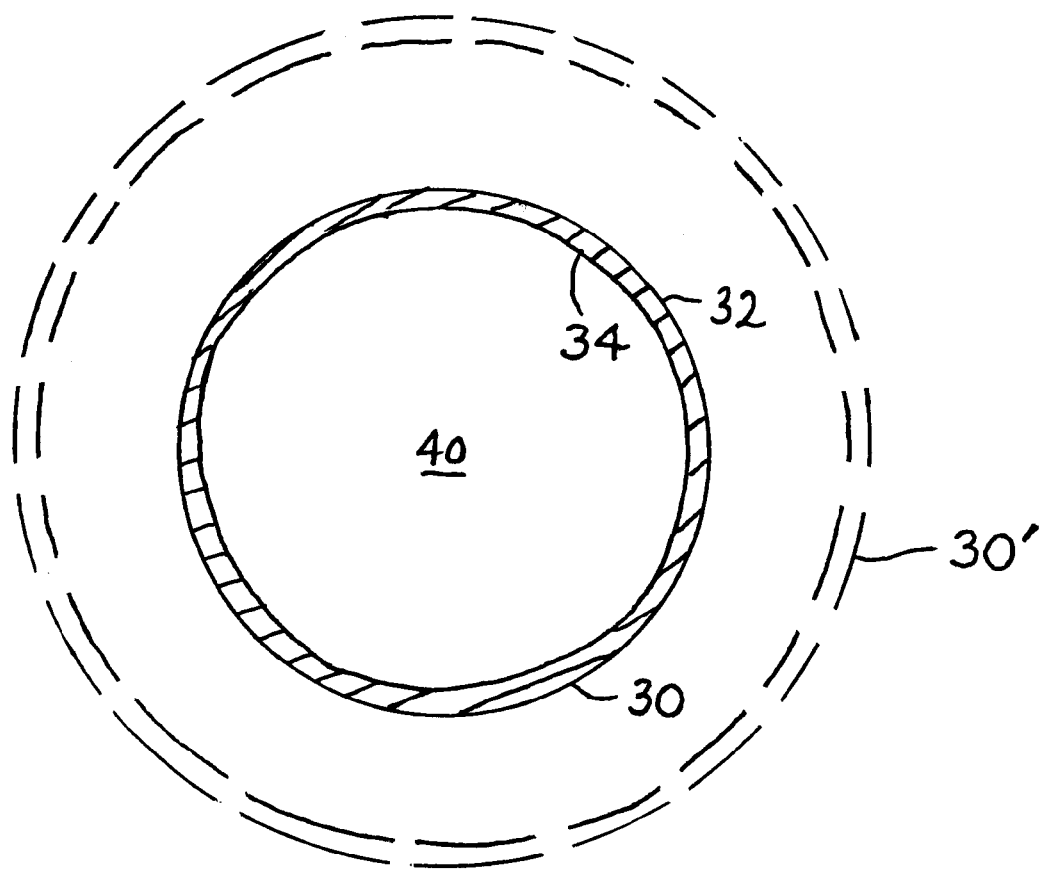
FIG. 4 is a cross-sectional transverse view of a balloon according to one embodiment of the invention, with a corresponding depiction of same in dashed line representation showing the balloon as inflated in use.

FIG. 4 is a cross-sectional transverse view of a balloon 30 according to one embodiment of the invention, with a corresponding depiction of same in dashed line representation showing the balloon 30' as inflated in use.

The balloon 30 as illustrated has an interior surface 34 bounding an interior lumen 40 of the balloon, and an exterior surface 32, with the interior and exterior surfaces defining a wall thickness of the balloon therebetween.

The balloon is inflated by introduction of pressurized gas into the lumen 40 in use of the balloon, or otherwise by imposing a pressure differential across the thickness of the wall of the balloon inducing the expansion of the balloon's lumenal volume. The balloons in accordance with the present invention are usefully employed in both high pressure and low pressure applications. The walls of the balloon are sufficiently thin to allow the balloon to be collapsed by deflation sufficiently to permit passage into and through the artery, vein or other lumenal passageway involved in the procedure.

As will be obvious to those skilled in the art, the balloons of the invention can also be employed to replace balloons in any of the many other types of balloon-catheter combinations, with or without guide wires, currently employed in medical dilatation procedures. The balloons of the invention possess properties that render them especially valuable in carrying out various types of in vivo lumenal procedures.

The rigidity or "set" of the cross-linked product article of the invention is adequate to permit ready flexural and translational movement of the article, with resilient recovery of the original shape when the flexural or translational force is removed.

The polyurethane balloon of the invention therefore can be embodied in a high pressure balloon, as a semicompliant product having a low profile or sleeve shape that can expand to a desired radius when inflated, and when deflated, reverts to the original low profile shape, with the ability to accommodate interior pressurization pressure levels of 4–6 atmospheres. By controlled cross-linking of the balloon of a selected profile, a semicompliant (wall of the) balloon is produced that will expand to a certain volume and then stop inflating, commensurate with the cross-linking density of the film. Concomitantly, the balloon when deflated will return to its original shape or retract to the original shape without the problem of winging.

Alternatively, the polyurethane balloon of the invention can be embodied in a low pressure balloon having low creep and high elasticity characteristics. By controlled cross-linking one can minimize or eliminate the creep problem otherwise associated with (uncross-linked) polyurethane balloons, and when the balloon is deflated, it retracts to the original shape of the balloon.

Although the invention has been variously disclosed herein with reference to illustrative aspects, embodiments and features, it will be appreciated that the aspects, embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A balloon article comprising a balloon formed of a partially UV-cross-linked polyurethane material and having an exterior surface, wherein said balloon has a cross-linking density that is substantially uniform throughout at least said exterior surface.

2. The balloon article of claim 1, wherein the partially UV-cross-linked polyurethane material has a % crosslinking in the range of from about 5% to about 90%.

3. The balloon article of claim 1, wherein the partially UV-cross-linked polyurethane material has a % crosslinking in the range of from about 20% to about 80%, for high pressure usage in which the balloon is inflated to a pressure in the range of from about 4 to about 6 atmospheres.

4. The balloon article of claim 1, wherein the partially UV-cross-linked polyurethane material has a % crosslinking in the range of from about 5% to about 50%, for low pressure usage in which the balloon is inflated to a pressure in the range of from about 1 to about 5 psi.

5. The balloon article of claim 1, wherein the balloon has a wall thickness of said UV-cross-linked polyurethane material in the range of from about 0.01 mm to about 0.5 mm.

6. The balloon article of claim 1, wherein the balloon has an internal diameter in the range of from about 1 mm to about 30 mm.

7. The balloon article of claim 1, wherein the balloon is coupled to a catheter communicating in closed flow communication with an interior volume of the balloon.

8. The balloon article of claim 7, wherein the balloon is integrally formed with the catheter.

9. The balloon article of claim 7, wherein the balloon is bonded to the catheter.

10. The balloon article of claim 1, wherein the balloon is formed by partially crosslinking a homogeneous composition upon exposure to ultraviolet radiation, wherein said homogeneous composition comprises a UV-cross-linkable polyurethane material, a cross-linker component that is cross-linkable by free-radical polymerization, and a free-radical source material generating free radicals in exposure to ultraviolet radiation, wherein the ultraviolet radiation is arranged to be substantially uniform over said exterior surface of said balloon, and wherein said balloon article is resiliently deformable from and resiliently recoverable to an initial shape of the article.

11. The balloon article of claim 10, wherein the homogeneous composition further comprises a radiopaque filler.

12. The balloon article of claim 11, wherein the radiopaque filler comprises a filler selected from the group consisting of barium sulfate, bismuth trioxide, bismuth oxychloride, bismuth subcarbonate, tungsten powder, and combinations of two or more of the foregoing.

13. The balloon article of claim 10, wherein the homogeneous composition further comprises one or more components selected from the group consisting of UV stabilizers, antioxidants, colorants, pigments, non-radiopaque fillers, and compatible combinations of two or more of the foregoing.

14. The balloon article of claim 10, wherein the cross-linker component comprises one or more of compounds containing functional groups selected from the group consisting of acryl, (meth) acryl, vinyl, propenyl, butenyl, pentenyl, hexenyl, octenyl, allyl, alkenyloxy, alkenylamino, allyloxy, allylamino, furanyl, phenyl and benzyl.

15. The balloon article of claim 10, wherein the cross-linker component is selected from the group consisting of triallyl cyanurate, trimethylolpropane triacrylate, and melamine cross-linkers.

16. The balloon article of claim 10, wherein the free radical source material comprises one or more of benzoin, substituted benzoins, benzopheone, benzopheone derivatives, Michler's ketone, alphahydroxyketone, benzildimethylketal, isopropylthioxanthane, dialkoxyacetophenones, acetophenone, benzil, and other derivatives (substituted forms) and mixtures thereof.

17. The balloon article of claim 10, wherein the cross-linker component comprises trimethylol propane triacrylate or triallylcyanurate, and the free-radical source material comprises benzophenone or benzildimethylketal.

18. A method of fabricating a balloon article as in claim 1 for in vivo lumenal use, comprising the steps of: forming a precursor structure for the balloon article, wherein said precursor structure comprises a homogeneous composition including a cross-linkable polyurethane material, a cross-linker component that is cross-linkable by free-radical polymerization, and a free-radical source material generating free radicals in exposure to ultraviolet radiation, and exposing the precursor structure to ultraviolet radiation for sufficient time and under sufficient radiation intensity to partially cross-link the homogeneous composition, provided that the radiation intensity is substantially uniform over an exterior surface of said precursor structure, to yield the balloon article.

19. The method of claim 18, wherein the homogeneous composition further comprises one or more components selected from the group consisting of UV stabilizers, antioxidants, colorants, pigments, non-radiopaque fillers, and compatible combinations of two or more of the foregoing.

20. The method of claim 18, wherein the cross-linker component comprises one or more of compounds containing functional groups selected from the group consisting of acryl, (meth) acryl, vinyl, propenyl, butenyl, pentenyl, hexenyl, octenyl, allyl, alkenyloxy, alkenylamino, allyloxy, allylamino, furanyl, phenyl and benzyl.

21. The method of claim 18, wherein the cross-linker component is selected from the group consisting of triallyl cyanurate, trimethylolpropane triacrylate, and melamine cross-linkers.

22. The method of claim 18, wherein the free radical source material comprises one or more of benzoin, substituted benzoins, benzopheone, benzopheone derivatives, Michier's ketone, alphahydroxyketone, benzildimethylketal, isopropylthioxanthane, dialkoxyacetophenones, acetophenone, benzil, and other derivatives (substituted forms) and mixtures thereof.

23. The method of claim 18, wherein the homogeneous composition as partially cross-linked upon exposure to ultraviolet radiation has a % crosslinking in the range of from about 5% to about 90% respectively.

24. The method of claim 18, wherein the homogeneous composition as partially cross-linked upon exposure to ultraviolet radiation has a % crosslinking in the range of from about 20% to about 80%, for high pressure usage in which the balloon is inflated to a pressure in the range of from about 4 to about 6 atmospheres.

25. The method of claim 18, wherein the homogeneous composition as partially cross-linked upon exposure to ultraviolet radiation has a % crosslinking in the range of from about 5% to about 50%, for low pressure usage in which the balloon is inflated to a pressure in the range of from about 1 to about 5 psi.

* * * * *

UNITED STATES PATENT AND TRADEMARK OFFICE
CERTIFICATE OF CORRECTION

PATENT NO. : 6,663,646 B1
DATED : December 16, 2003
INVENTOR(S) : Shah

It is certified that error appears in the above-identified patent and that said Letters Patent is hereby corrected as shown below:

<u>Title page,</u>
Item [57], ABSTRACT,
Line 1, "in vivo" should be -- *in vivo* --

<u>Column 10,</u>
Line 10, "in vivo" should be -- *in vivo* --

Signed and Sealed this

Twenty-fourth Day of February, 2004

JON W. DUDAS
*Acting Director of the United States Patent and Trademark Office*